US009655512B2

(12) United States Patent
Huang et al.

(10) Patent No.: US 9,655,512 B2
(45) Date of Patent: May 23, 2017

(54) METHODS AND SYSTEMS TO MEASURE CORNEAL EPITHELIAL THICKNESS AND POWER, STROMAL THICKNESS, SUBEPITHELIAL CORNEAL POWER AND TOPOGRAPHY FOR DISEASE DIAGNOSIS

(75) Inventors: David Huang, Portland, OR (US); Yan Li, Portland, OR (US); Ou Tan, Portland, OR (US); Maolong Tang, Portland, OR (US)

(73) Assignee: UNIVERSITY OF SOUTHERN CALIFORNIA, Los Angeles, CA (US)

(*) Notice: Subject to any disclaimer, the term of this patent is extended or adjusted under 35 U.S.C. 154(b) by 1198 days.

(21) Appl. No.: 13/441,733

(22) Filed: Apr. 6, 2012

(65) Prior Publication Data

US 2013/0128222 A1    May 23, 2013

Related U.S. Application Data

(60) Provisional application No. 61/473,673, filed on Apr. 8, 2011.

(51) Int. Cl.
*A61B 3/107* (2006.01)
*A61B 3/10* (2006.01)
*G06T 7/60* (2017.01)

(52) U.S. Cl.
CPC .............. *A61B 3/1005* (2013.01); *G06T 7/60* (2013.01); *G06T 2207/10101* (2013.01); *G06T 2207/30041* (2013.01)

(58) Field of Classification Search
CPC . G06T 7/60; G06T 7/602; G06T 2207/10101; G06T 2207/30041; A61B 3/1005; A61B 3/102
See application file for complete search history.

(56) References Cited

U.S. PATENT DOCUMENTS

| | | | |
|---|---|---|---|
| 2004/0263785 A1* | 12/2004 | Chernyak | A61B 3/1015 351/246 |
| 2007/0282313 A1* | 12/2007 | Huang | A61B 3/1005 606/5 |
| 2009/0316112 A1* | 12/2009 | Neal | G06T 5/50 351/246 |
| 2011/0032533 A1* | 2/2011 | Izatt | G01B 11/2441 356/497 |
| 2011/0149239 A1* | 6/2011 | Neal | A61B 3/0025 351/205 |
| 2012/0133887 A1* | 5/2012 | Huang | A61B 3/102 351/206 |
| 2012/0249962 A1* | 10/2012 | Uchida | A61B 3/102 351/208 |

* cited by examiner

*Primary Examiner* — George Evanisko
(74) *Attorney, Agent, or Firm* — DLA Piper LLP (US)

(57) ABSTRACT

This invention discloses methods and systems for measuring corneal epithelial thickness and power, stromal thickness, subepitheila corneal power and topography. The systems and methods disclosed herein are non-invasive, non-contact and automated imaging methods which preferably makes use of Fourier-domain optical tomography. Also disclosed herein are scanning patterns and image analysis methods for utilizing and analyzing Fourier-domain optical coherence tomography images to obtain information about conical epithelial and stromal properties as well as parameters useful for evaluating the properties. The methods and systems described herein are useful as eye disease diagnostic tools and eye surgery planning tools.

7 Claims, 12 Drawing Sheets

An average axial-scan

METHODS AND SYSTEMS TO MEASURE CORNEAL EPITHELIAL THICKNESS AND POWER, STROMAL THICKNESS, SUBEPITHELIAL CORNEAL POWER AND TOPOGRAPHY FOR DISEASE DIAGNOSIS

CROSS-REFERENCE TO RELATED APPLICATIONS

This application claims the benefit of U.S. Provisional Application No. 61/473,673 filed Apr. 8, 2011, which is incorporated herein by reference in its entirety.

STATEMENT REGARDING FEDERALLY SPONSORED RESEARCH AND DEVELOPMENT

The present invention is made, at least in part, with the support of NIH grant R01EY018184. The government has certain rights in the invention.

FIELD OF THE INVENTION

The invention pertains to the field of ophthalmology. More particularly, the invention pertains to methods and systems for measuring corneal epithelial thickness and power, stromal thickness, subepithelial corneal power and topography as well as methods for diagnosing eye diseases utilizing said measuring methods and systems.

BACKGROUND OF THE INVENTION

Figure 1:
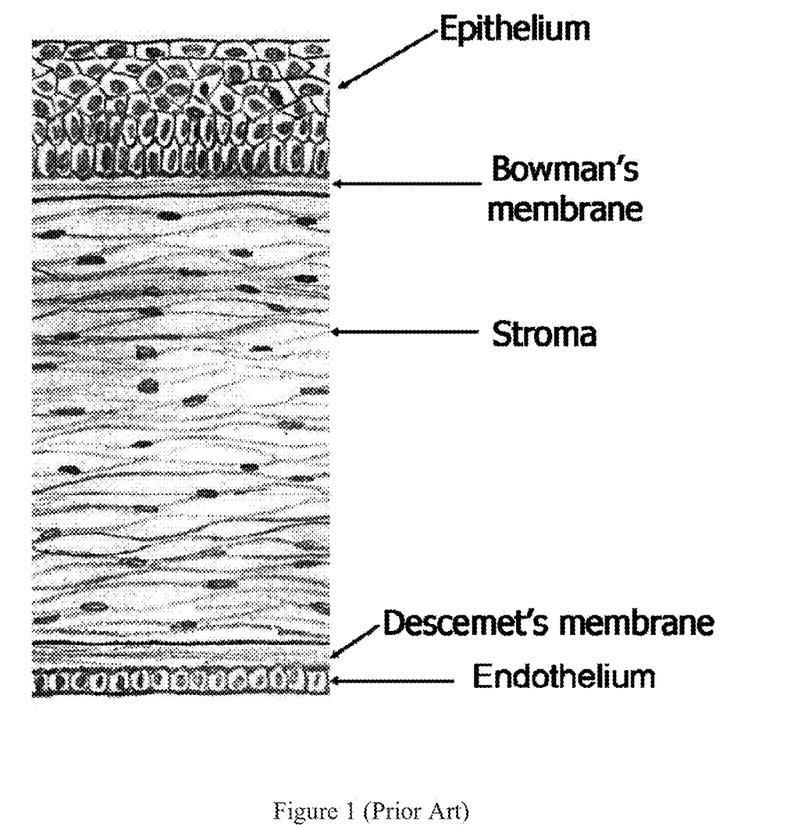
FIG. 1 shows the anatomy of the cornea.

The human corneal epithelium covers the front of the cornea and protects the eye (FIG. 1). It is made up of epithelial tissue and normally has five to six cell layers.[1] Corneal epithelium is a self-renewing tissue. It's highly active and a complete turnover takes place in approximately a week.[2] Corneal epithelium is able to alter its thickness to mask sub-epithelial stromal irregularities and maintain a smooth optical surface of the eye.[3] In diseases such as keratoconus, the thickness of the epithelium becomes altered to reduce corneal surface irregularity. Therefore, the presence of an irregular stroma may be less measurable by frontal surface corneal topography. Analyzing the corneal epithelium and stroma thickness and shape separately can facilitate the detection of the disease in its early stage.

On the other hand, corneal epithelium contributes to the total corneal power due to its thickness profile and the difference in refractive index between epithelium and stroma (1.401 vs 1.380).[4] In laser corneal surgeries, the common way to perform photorefractive keratectomy (PRK) or phototherapeutic keratectomy (PTK) is to remove the epithelium first. Therefore, it is useful to measure the corneal topography and power under the epithelium for the purpose of planning PRK/PTK surgeries. Moreover, epithelial smoothing following laser keratorefractive surgery such as PRK or LASIK has been modeled mathematically.[3] What is still needed is the capability to map the corneal epithelium. This can aid in the understanding of epithelial thickness modulation after ablation. Eventually this knowledge may help minimize the regression after surgery and the aberration induced by the surgery.

To this end, different methods, such as optical coherence tomography (OCT), confocal microscopy and optical pachymetry and confocal microscopy have been used to measure corneal epithelial thickness. Many of these studies measured average central epithelium thickness. Some studies used OCT or confocal microscopy to measure peripheral epithelium thickness, but the number of points measured in the periphery was limited[5-7] and the measurement was very time consuming.[5] Ultrahigh frequency ultrasound imaging (Artemis by Ultralink, Inc.) can also map corneal epithelium and stromal thickness.[8-13] However, it requires immersing the eye in a fluid bath because ultrasound cannot pass through air. The inconvenience and discomfort associated with the fluid bath makes it unsuitable for clinical applications.

Optical coherence tomography (OCT) is a non-contact imaging technique based on principles of low-coherence interferometry.[14] Its high axial resolution allows better delineation of the anterior and posterior surfaces of the cornea. Time-domain anterior segment OCT systems capable of generating pachymetry (corneal thickness) maps have been reported.[15,16] However, time-domain OCT still suffers from slow speed which makes it susceptible to eye movements during image acquisition.

Recently, a newer generation of OCT known as Fourier-domain OCT (FD-OCT) has been made available. This new generation of OCT has acquisition speeds 10-100 times faster than time-domain OCT systems.[17-19] The very high scan speed may minimize the effect of eye movement during data acquisition while obtain dense sample points over the cornea. Although promising, acquiring and analyzing data using FD-OCT is not trivial. No known method of using FD-OCT to generate corneal epithelial and/or stromal map has heretofore been reported.

In view of the above, there still exists a need for a fast, reliable, and convenient method that is suitable for clinical measurement of corneal epithelium and/or stromal properties such as thickness and refractive power. There are many clinical utilities for such measurements. One particular application that can benefit from such a method is keratoconus.

Keratoconus is an important contraindication for refractive surgeries such as LASIK. Undetected corneal ectatic disorders can result in accelerated, progressive keratoectasia and produces poor vision that cannot be corrected with spectacles.

The National Eye Institute reports that keratoconus is the most common corneal dystrophy in the United. States, affecting approximately 1 in 2,000 Americans, but some reports place the figure as high as 1 in 500. In keratoconus, the normally round basketball-shaped cornea progressively thins and becomes football shaped causing a cone-like bulge to develop, and slight blurring and distortion of vision and increased sensitivity to light in its earliest stages. In later stages, it causes decreased visual acuity and significant visual impairment, which makes simple tasks, like driving, watching TV or reading a book nearly impossible.

Moderate to advanced keratoconus is easily recognizable by several distinctive clinical features, but the diagnosis of early stage keratoconus can be very challenging.[22] Surgeons learned to better recognize the early stage keratoconus (referred to as forme fruste keratoconus or FFK in medical literature) on corneal topography.[23,24] However, topography does not screen out all eyes at risk. Topography measures only anterior topographic distortion. But keratoconus is also characterized by posterior topographic steepening, focal corneal thinning, and focal epithelial thinning. Detecting these changes with OCT could improve risk assessment and thus reduce the incidence of post-LASIK ectasia.

SUMMARY OF THE INVENTION

As explained above, prior art methods of mapping corneal epithelial and stromal properties such as epithelial thickness all suffer from various shortcomings that prevented them from being widely adopted in clinical use. Accordingly, it is an object of the present invention to provide a clinically applicable method for measuring corneal epithelium and stromal properties.

Although Fourier-domain optical coherence tomography represents a significant improvement over time-domain OCT, processing and analyzing the resulting image data is not trivial. It was not clear from the outset whether FD-OCT could generate reliable data for determining corneal epithelial and stromal properties such as corneal epithelial thickness, corneal stromal thickness, corneal epithelial power, subepithelial corneal topography, subepithelial corneal power, and the like. It was also not clear whether suitable methods could be developed to analyze the data so as to yield meaningful diagnostic information in a clinically acceptable format. In the present invention, it was discovered that using a combination of scanning patterns and data analysis methods, corneal epithelial and stromal properties could be reliably determined for clinical use.

Therefore, in one aspect, the present invention provides an automated non-contact method for mapping a corneal epithelial and stromal property of a subject. Methods in accordance with this aspect of the invention will generally include the steps of generating corneal images of the subject by scanning the subject's cornea with a Fourier-domain optical coherence tomography imaging device configured to scan the cornea with a predetermined pattern; analyzing the scanned images to determine structural boundaries of the cornea; and computing a corneal and stromal property.

As used herein, the term "non-contact" means that the method does not require physical contact between the cornea and the measuring device. For example, in ultrafrequency ultrasound pachymetry, the subject's cornea is immersed in a water bath in order for the ultrasound waves to make physical contact with the cornea. This is considered "contact" in the context of the present invention. In contrast, in optical coherence tomography, light is used as the probing signal so that no physical contact is necessary between the OCT device and the cornea. This is considered "non-contact" in the context of the present invention.

As used herein, the terms "corneal epithelial property" and "corneal stromal property" refer to measurable structural and functional properties associated with the cornea. Exemplary corneal epithelial and stromal properties may include epithelial thickness map, corneal epithelial power, corneal stromal thickness map, subepithelial corneal topography map, subepithelial corneal power and combinations thereof.

When generating the corneal images, each scan may be repeated multiple times using the same scanning pattern so as to generate duplicate scans that may be used in later processing to enhance image quality or to detect eye movement during scans. Preferably, each scan is repeated about 3 to about 5 times.

Figure 2:
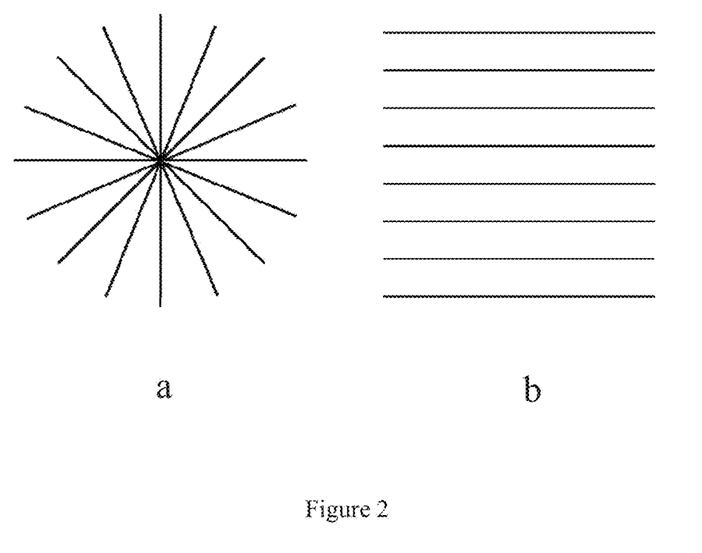
FIG. 2a shows a scan pattern according to one embodiment of the present invention that is 8 radial (6 mm scan length, 1024 axial scans each) and is to be repeated for 5 times.
FIG. 2b is an example of a raster scan pattern (evenly distributed line scans) as an alternative scan pattern to be used in connection with the present invention.

Scanning pattern is a key element that enables FD-OCT to reliably determine corneal epithelial and stromal properties. Ideally, a suitable scanning pattern should provide sufficient data density and distribution over the cornea. In one preferred embodiment, the scanning pattern is a radial spoke pattern having N radial scans arranged in a radial spoke line pattern as shown in FIG. 2a. In another preferred embodiment, the number N can be any even number larger or equal to 4. In another alternative embodiment, the scanning pattern is a raster pattern as shown in FIG. 2b.

Figure 12:
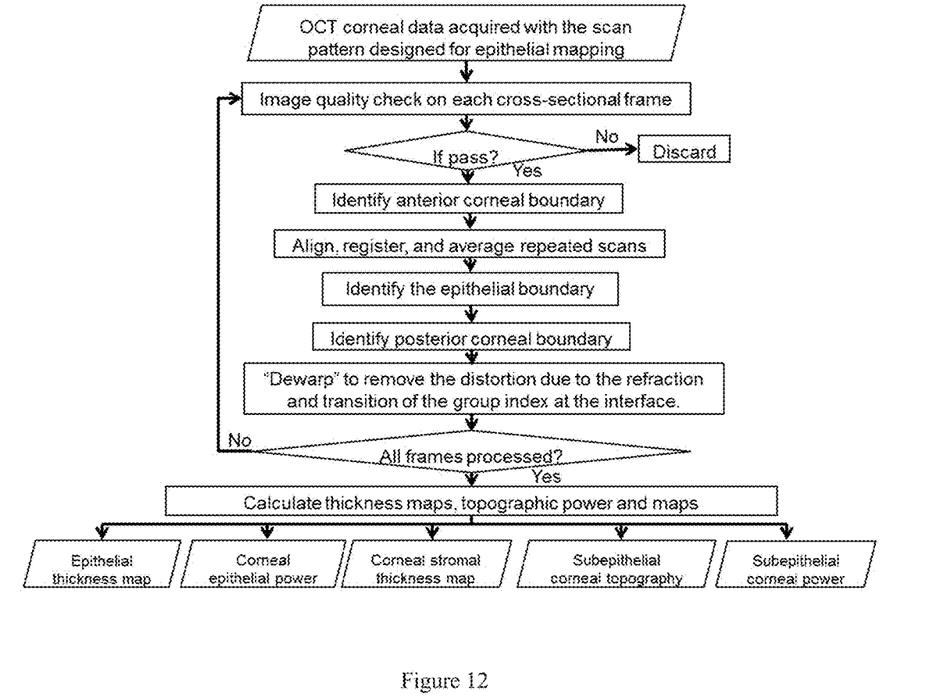
FIG. 12 shows a flowchart illustrating an exemplary method for measuring corneal epithelial/stromal thickness and power in accordance with embodiments of this invention.

Analysis of the acquired image is preferably performed automatically by a processing unit such as a PC or an integrated processing unit within the FD-OCT device. FIG. 12 illustrates an exemplary algorithm for analyzing the images. Briefly, analysis of the acquired images may have the following general steps:
 a. checking image quality of each scanned image, and accepting the image for further processing only when the image passes the quality check;
 b. identifying anterior corneal boundary on the image;
 c. aligning, registering and averaging repeated scans;
 d. identifying the epithelial boundary;
 e. identifying the posterior corneal boundary;
 f. dewarping the image to remove distortions; and
 g. repeat steps a through e until all images have been analyzed The epithelial boundary may be identified with any suitable method of boundary identification known in the art. In a preferred embodiment, a progressive scheme of identifying the epithelial boundary is used.

Because OCT imaging systems use laser light to probe the bio-tissue, therefore, they are subject to the effects of refraction at surfaces corresponding to interfaces between regions of differing refractive index. To accurately determine the thickness, curvature, refractive power of the cornea and its sublayers, a "Dewarping" procedure is performed to remove the OCT image distortions due to the refraction and transition of the group index at the interface.

In another aspect, the present invention also provides a method for planning an eye surgery or diagnosing an eye disease. Methods in accordance with this aspect of the invention will generally include the steps of acquiring cornea images using a Fourier-domain optical coherence tomography device; processing the acquired corneal images to determine a corneal epithelial and/or a corneal stromal property; determining a diagnosis of an eye disease or generating a plan for an eye surgery based on the corneal epithelial and/or stromal properties. Acquisition and analysis of FD-OCT scan images are as described above.

As noted in the background section, corneal epithelium contributes to the total corneal power due to its thickness profile and the difference in refractive index between the epithelium and the stroma. Vision corrective surgeries such as photorefractive keratectomy (PRK) and phototherapeutic keratectomy (PTK) involve removing the epithelium and reshaping the optical property of the cornea. Information about the topography and power under the epithelium is therefore extremely useful for guiding PRK and PTK surgeries. In ectatic eye diseases such as keratoconus, epithelium thinning is a good indicator for the location of the keratoconic cone, hence, information about the corneal epithelium may provide valuable diagnostic information.

In a further aspect, the present invention also provides a system for mapping the corneal epithelial and stromal thickness of a subject. Systems in accordance with this aspect of the invention will generally include a FD-OCT device configured to scan the cornea of a subject using a scanning pattern as described herein; and a processing unit configured to perform the processing and analysis method described above.

In yet another aspect, the present invention also provides a computer implemented method for evaluating non-uniformity in a corneal epithelial map. Methods in accordance with this aspect of the invention will generally include the steps of analyzing the corneal epithelial map to compute a value for one or more evaluative parameters, wherein the parameters provide a quantitative evaluation of the degree to which the corneal epithelium is irregular. Exemplary evaluative parameters may include thickness asymmetry, thinning and local thinning, root-mean-square variation, root-mean-square pattern deviation, or any combination thereof, but are not limited thereto. Computational details for these parameters are more fully described in the Detailed Descriptions section below.

Because evaluation methods in accordance with this aspect of the invention works directly on corneal epithelial maps, they are not particularly limited to images generated by a FD-OCT device but are generally applicable to images of the cornea generated by any presently known or future invented mapping means capable of providing corneal epithelial maps with sufficient resolution and precision. For example, maps generated by ultrahigh frequency ultrasound pachymetry may also be evaluated using these methods. Preferably, the resolution of the map is at least 5 µm.

In still another aspect, the present invention also provides a computer implemented method for characterizing and quantifying focal thinning and focal bulging caused by keratoconus. Methods in accordance with this aspect of the invention will generally include the step of fitting a corneal epithelial and/or stromal variables to mathematical functions; and using the fitted mathematical functions to represent the qualitative and quantitative characteristics of the cornea's epithelium and/or stroma. Suitable mathematical functions are those having graphs shaped like a cone with higher values at the center and lower values away from the center. The epithelial/stromal variable being fitted could be inverse thickness or normal thickness minus the actual thickness. In some preferred embodiments, epithelial thickness may be fitted to inverse Gaussian. In other preferred embodiments, the corneal epithelial and stromal maps are fitted to Gaussian functions for characterization and quantification.

Moreover, methods in accordance with this is aspect of the invention may be implemented with any computational means commonly known in the art. For example, implementation may take the form of a custom computer chip or a software written in any suitable programming language such as Matlab, C, C++, Fortran, etc.

While the above described embodiment outlines the general steps of the present invention, it will be understood by those skilled in the art that various modifications are possible. Other aspects and advantages of the present invention will become apparent from the following detailed description and the appended claims.

DETAILED DESCRIPTION

Optical Coherence Tomography (OCT) is a technique known to those of ordinary skill in the art. The systems of the present invention may be implemented by adapting a conventional OCT system to carry out the methods more fully described below. Suitable OCT systems include a Fourier-domain OCT system (RTVue-CAM, Optovue, Inc., Fremont, Calif.) capable of acquiring 26,000 axial-scans per second. It has an axial resolution of 5 µm in cornea. Other OCT systems with proper scan speed and axial resolution may also be used for corneal epithelium and stroma mapping and carrying out the methods described herein.

At minimum, the systems of the present invention include a data processing system operably coupled to or operably incorporated into an OCT system. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities).

Another embodiment of the present invention is an article of manufacture, such as a computer program product comprising a non-transitory computer readable medium having a computer readable code embodied in the medium, the computer readable program code in the article of manufacture comprising computer readable program code means for causing the computer to perform the methods of the present invention.

I. A Non-Contact and Automatic Method to Measure the Corneal Epithelial and Stromal Thickness and Power Scan Patterns A design of scan pattern was conceived for automatic corneal epithelium and stroma measurements. The scan pattern is a combination of N spoke like radial scans (N=4, 6, 8, 10, 12, . . . , 2n). The radial scans will be evenly distributed 180/N degree apart. Each radial scan contains equal number of axial scans. For a 6 mm long radial scan, a minimum of 512 axial scan is recommended. The scan pattern can be repeated M times (M=1, 2, 3, . . . , m) in one scan acquisition for purposes such as performing scan average or detecting eye movement. The scan pattern used in this example (FIG. 2a) is 8 radial (6 mm scan length, 1024 axial scans each) to be repeated for 5 times. Various imaging modalities such as OCT or ultrasound can benefit from this scan design.

An alternative design is to use raster scan patterns (evenly distributed line scans). An example of the raster scan pattern is shown in FIG. 2b.

Corneal Epithelial Thickness Map

According to some embodiments of the present invention, a Fourier-domain OCT system (RTVue-CAM, Optovue, Inc., Fremont, Calif.) capable of acquiring 26,000 axial-scans per second was used. It has an axial resolution of 5 μm in cornea. Other OCT systems with proper scan speed and axial resolution may also be used for corneal epithelium and stroma mapping.

Figure 3:
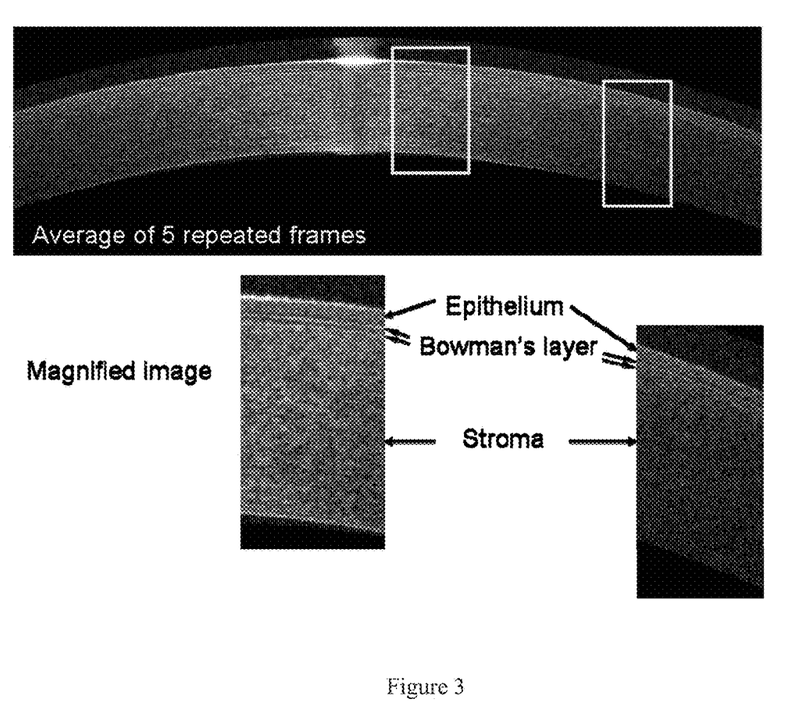
FIG. 3 shows an example of a meridianal cross-sectional OCT corneal image.

A pachymetry scan pattern (8 radials, 1024 axial-scans each, 6 mm diameter, repeat 5 times) was used to image the cornea (FIG. 2a). The scan pattern may be centered at the pupil center or corneal vertex.[20] We recommend centering the scan pattern using pupil center as demonstrated here. A meridianal cross-sectional OCT corneal image was shown in FIG. 3.

Figure 4:
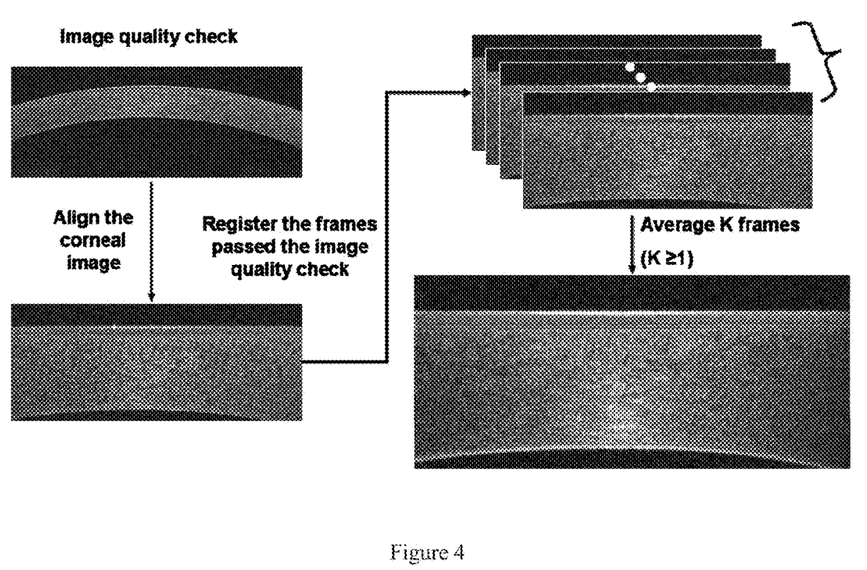
FIG. 4 shows that the K (K≥1) repeated radial scans on the same meridian are registered and averaged to increase the signal-to-noise ratio according to some embodiments.

An image quality check was first performed on each meridianal cross-sectional frame. Corneal images with low signal intensity, shadowing from the eye lash or lid, captured eye blinking or large eye movement during the scan acquisition were identified and excluded from the following analysis. Then the anterior corneal boundary was detected from each cross-sectional corneal image.[15] The axial-scans of the image were aligned to the anterior corneal surface. Next the K (K≥1) repeated radial scans on the same meridian were registered and averaged to increase the signal-to-noise ratio (FIG. 4).

Figure 5:
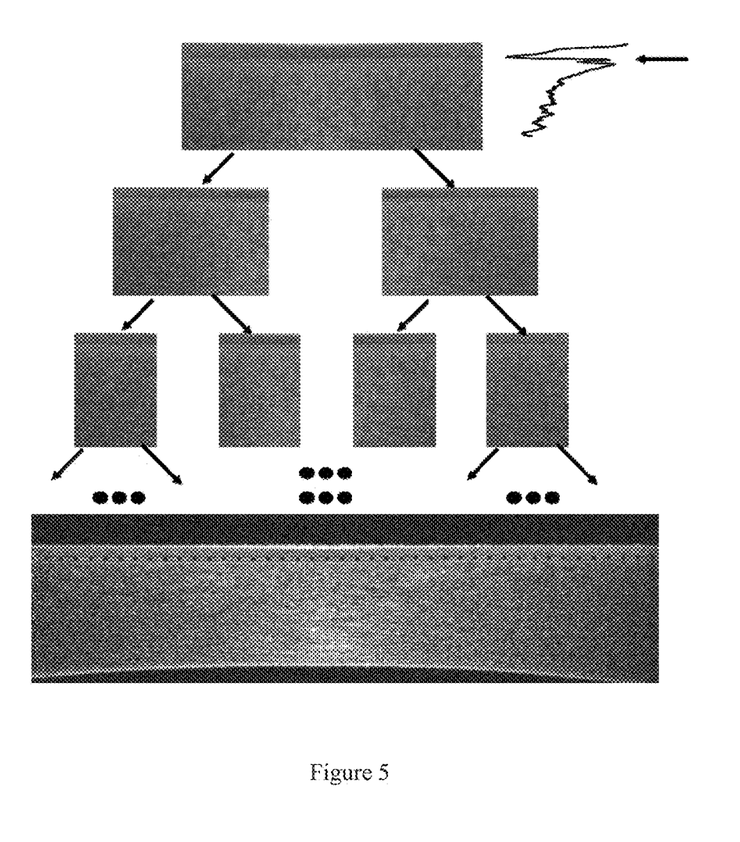
FIG. 5 shows an example of a progressive approach in identifying the epithelium.
Figure 6:
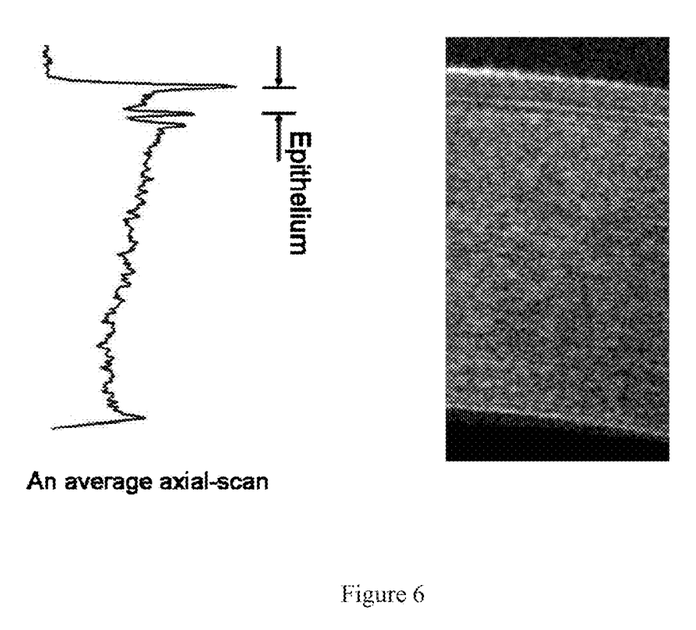
FIG. 6 shows an example of an averaged axial-scan that demonstrates the characteristics at the epithelial boundary.

A progressive scheme was used to identify the epithelial boundary in the image.[21] A summation axial-scan was first calculated from the aligned average corneal image. The initial epithelium boundary location was estimated by the increased signal intensity posterior to the anterior corneal surface. Then the image was divided into two sections (FIG. 5). The epithelium boundary location obtained in last step was used as the initial value to search the epithelium boundary location in the sub-images. An example averaged axial-scan was shown in FIG. 6 to demonstrate the characteristics at the epithelial boundary. This process may be repeated until $2^n$ axial-scans were in each sub-image, wherein n=0, 1, 2, 3 . . . . In one particular embodiment, the process was repeated until 8 axial-scans were in each sub-image. Then the epithelial boundary location in each sub-image was interpolated to acquire the entire epithelial boundary (FIG. 5).

Figure 7:
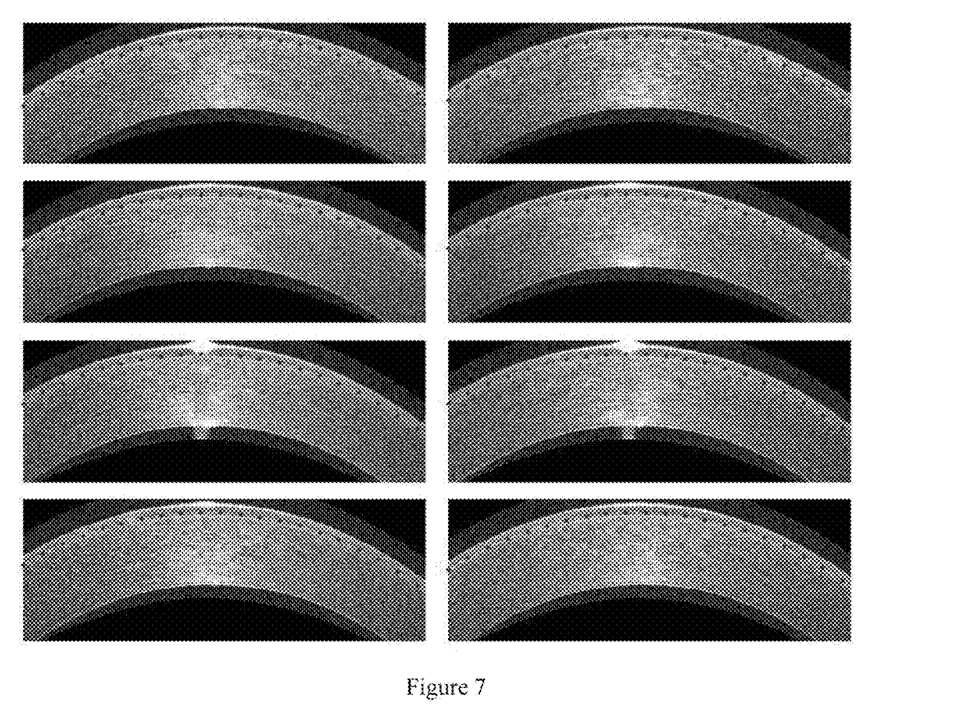
FIG. 7 shows examples shows examples of the epithelial profile for all eight meridians.
Figure 8:
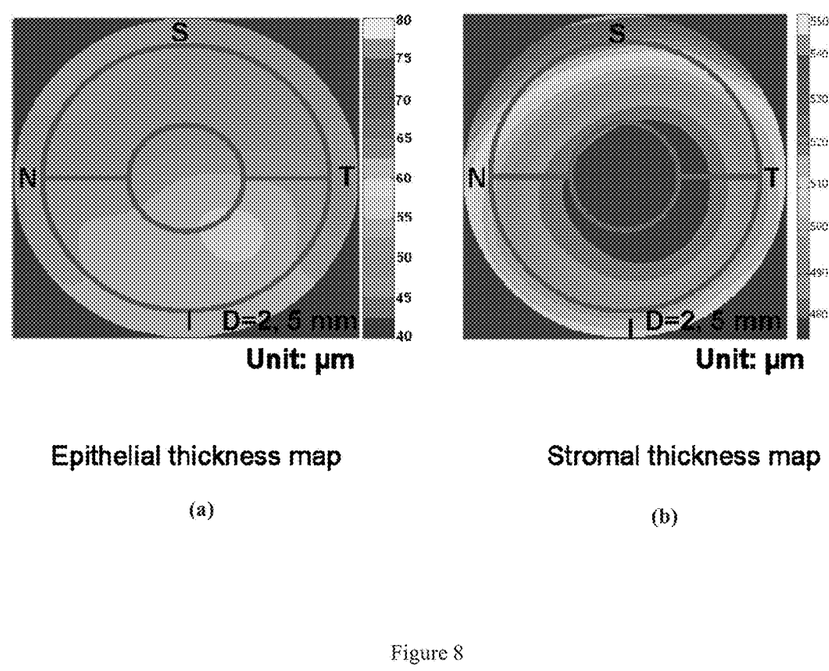
FIG. 8a shows an example of the epithelial thickness map generated by interpolating the epithelial thickness profile calculated from each meridian.
FIG. 8b shows an example of the corneal stromal thickness map generated by interpolating the stromal thickness profile calculated from each meridian.

This procedure was repeated for all eight meridians (FIG. 7). Epithelial thickness profile of each meridian were calculated after correcting the refraction and transition of the group index at the air-corneal interface with a "dewarping" method.[15] Then the epithelial thickness map was generated by interpolating epithelial thickness profile calculated from each meridian (FIG. 8a).

Corneal Stromal Thickness Map

The same scan pattern for measuring the corneal epithelium was used to measure the corneal stroma. The corneal stromal thickness was calculated by subtracting epithelial thickness from the corneal thickness. The automatic method to measure the corneal thickness has been developed previously.[15,20] The stromal thickness profile was first calculated for each meridianal cross-section image. Then the corneal stromal thickness map was generated by interpolating stromal thickness profile calculated from each meridian (FIG. 8b).

Corneal Epithelial Power and Subepithelial Corneal Power

The lenticular power of epithelium was calculated by subtracting the subepithelial corneal power (a.k.a. corneal power with epithelium off) from the corneal power. The subepithelial corneal power was calculated by averaging the central power of the epithelium boundaries from the radial scans assuming epithelium has been removed. The corneal power was calculated by averaging the central power of the air-corneal interfaces from the radial scans. In a keratoconic eye, for example, the subepithelial corneal power was calculated to be 48.33 D, and the corneal power was 47.13 D. Therefore, the lenticular power of epithelium was 47.13−48.33=−1.20 D.

The corneal epithelial power is useful in predicting the refractive effect of transepithelial photorefractive keratectomy (PRK) and transepithelial phototherapeutic keratectomy (PTK).

Subepithelial Corneal Topography

Figure 9:
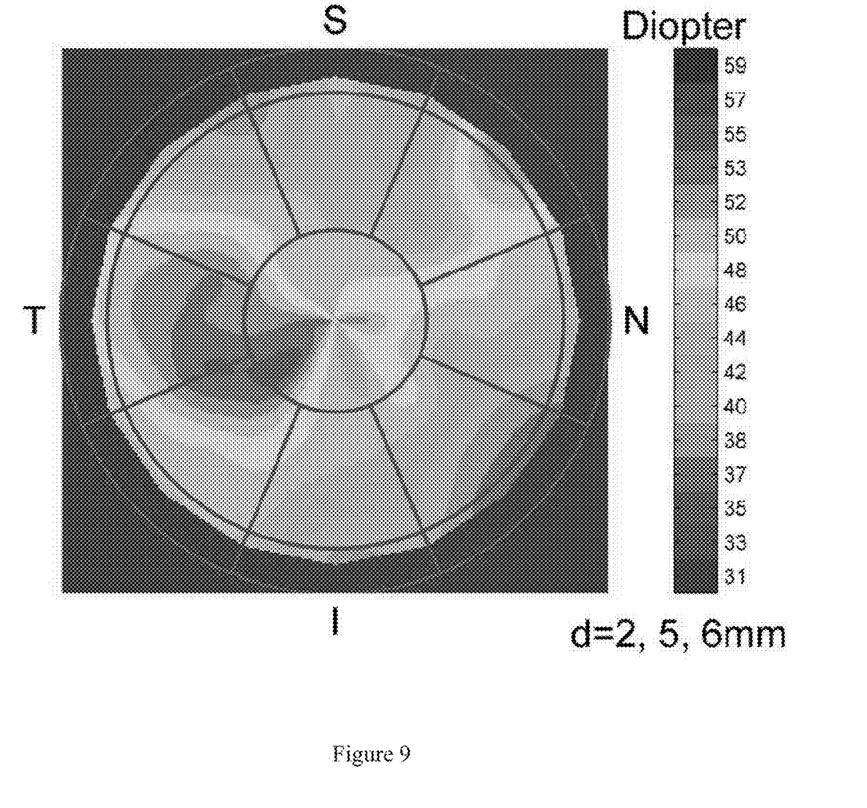
FIG. 9 show an example of a subepithelial topography map obtained in accordance with the present invention.

Subepithelial surface topography can be calculated based on the epithelial boundaries from the radial scans. The power on each individual point was calculated by fitting the epithelial boundaries and a topography map can be obtained by interpolation (FIG. 9).

Figure 10:
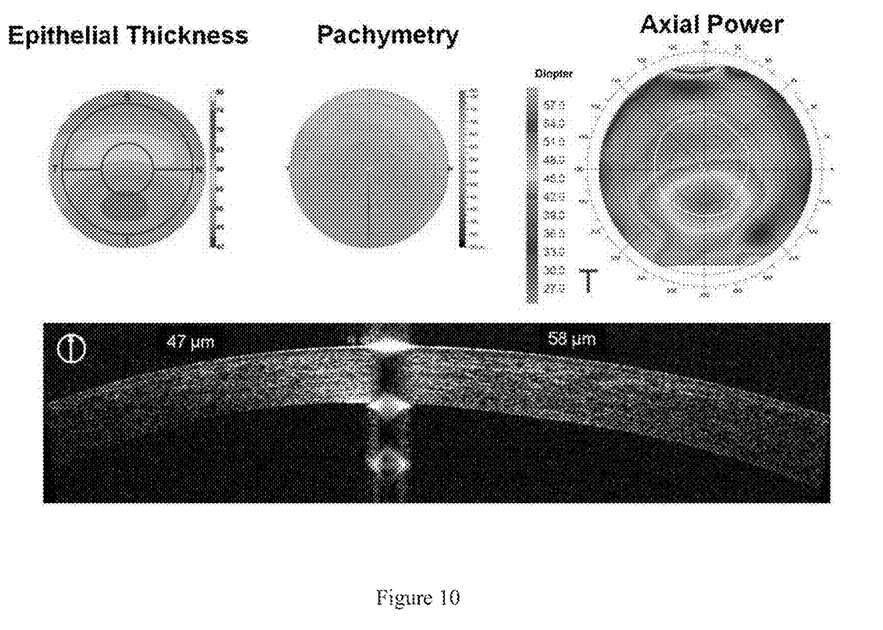
FIG. 10 shows an example of the observation of epithelium thinning over the cone.

Subepithelial corneal topography is useful in guiding PRK and PTK procedures in which the epithelium is removed mechanically or chemically (with ethanol solution) rather than by laser II. Corneal Maps for Keratoconus Diagnosis Reinstein et al. previously reported their study on corneal epithelium thinning over the kertatoconic cone with very-high frequency ultrasound.[8,10] However, in their study, ultrasound imaging was used to measure corneal epithelial thickness. As noted previously, ultrasound is not a non-contact method. Such method cannot be fully automated and is very inconvenient to perform for both the patient and the clinician. Moreover, Reinstein et al. only described epithelium thinning pattern in qualitative terms (e.g. epithelium thinning pattern has a "donut" shape over the cone in keratoconus) and provided some rudimentary statistics of the observed data (e.g. min, max, etc.). In the present invention, we have invented quantitative methods to evaluate the corneal epithelial map (FIG. 10) non-uniformity and pattern deviation. Our methods enables automated evaluation by computers.

Parameters to Evaluate the Corneal Epithelial Map Non-Uniformity

The corneal epithelial thickness was relatively uniform in normal subjects.[12] See the example described herein. Parameters were designed to evaluate the corneal epithelial map non-uniformity and pattern deviation in keratoconic eyes. Epithelial map size was limited to diameter 6 mm in this demonstration. The epithelial map was divided into annular zones with diameter of 2 and 5 mm. If the epithelial map has a larger size, more annular zones can be added, such as 7 or 10 mm.

Thickness Asymmetry of the Epithelial Map

The epithelial map was further divided into hemispheres or quadrants in addition to the annular zones. Superior minus inferior (S–I) asymmetry was calculated by the difference between average epithelial thickness of the superior hemisphere and inferior hemisphere inside diameter 2 and 5 mm areas. Superonasal minus inferotemporal (SN-IT) asymmetry was calculated by the difference between average epithelial thickness of the superonasal quadrant and inferotemporal quadrant inside the analytic zone.

Thinning and the Focal Thinning of the Epithelial Map

The minimum and maximum epithelial thicknesses were recorded, and the epithelial focal thinning was calculated as the difference between them.

Root-Mean-Square Variation of the Epithelial Map

The epithelial thickness map T can be represented as an N×N array. The origin (0, 0) was set at the center of the map. The values of the points located outside the circle of scan diameter were set to NaN (IEEE arithmetic representation for not-a-number) and won't be involved in calculation.

Root-mean-square variation (RMSV) from the average value of single epithelial thickness map was calculated as:

$$RMSV \text{ of the single epithelial map} = \sqrt{\frac{\sum_x \sum_y (\overline{T} - T(x,y))^2}{n}}.$$

Equation 1 where $\overline{T}$ was the average epithelial thickness inside diameter 5 mm area, $T(x,y)$ was the epithelial thickness at location (x, y) with $\sqrt{x^2+y^2} \le 2.5$ mm (inside d=5 mm area), n was the total number of the points on the map inside the diameter 5 mm area.

Root-Main-Square Pattern Deviation of the Epithelial Map

Root-mean-square deviation from the average epithelial thickness map of the normal population was calculated to evaluate the corneal epithelial map pattern deviation.

First, the epithelial pattern map of the normal reference population $P_N$ was calculated as $$P_N(x,y) = T_N(x,y)/\overline{T_N}$$

Equation 2 where $T_N$ was the average epithelial thickness map of a group of normal subjects (serve as a sample of the normal population), and $\overline{T_N}$ was the average thickness of map $T_N$.

Similarly, the individual epithelial pattern map P was calculated as $$P(x,y) = T(x,y)/\overline{T}$$

Equation 3 where T was the individual epithelial thickness map, and $\overline{T}$ was the average thickness of the map.

The epithelial pattern deviation map (PD) was calculated as the difference between the individual epithelial pattern map (P) and the average normal epithelial pattern map ($P_N$):

$$PD(x,y) = P(x,y) - P_N(x,y)$$

Equation 4

The root-mean-square pattern deviation (RMSPD) value was calculated from the pattern deviation map as $$RMSPD = \sqrt{\frac{\sum_x \sum_y (PD(x,y))^2}{N}}$$

Equation 5 where PD(x,y) was the epithelial pattern deviation value at map location (x,y). N was the total number of the map points inside the analytic zone.

Measuring Depth and Width of Focal Thinning on the Epithelial Map

Figure 11:
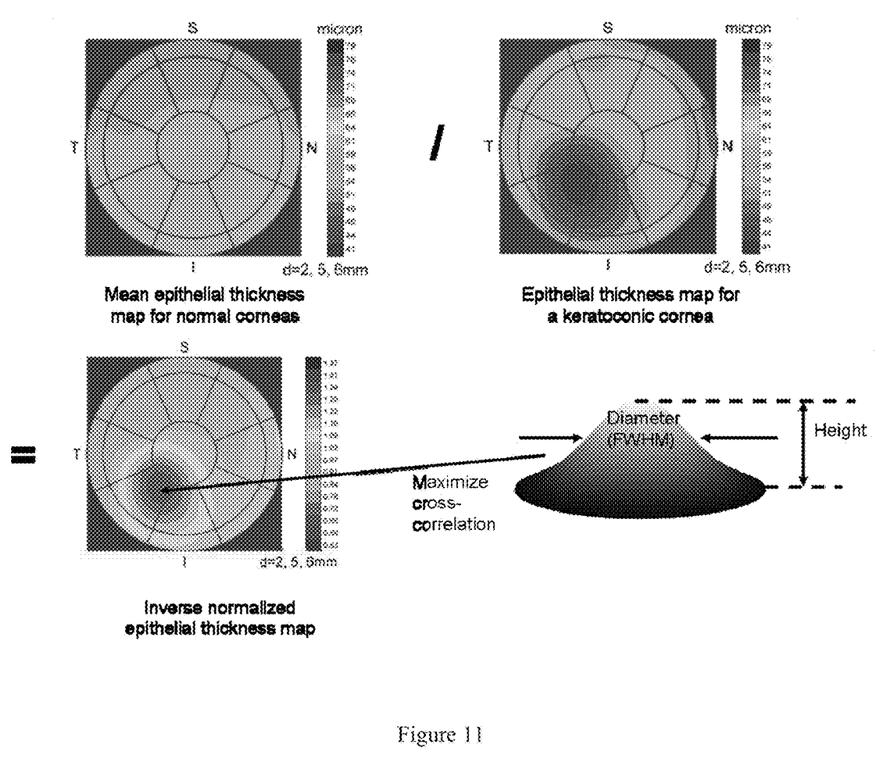
FIG. 11 shows the Gaussian fitting of on the epithelial map in accordance with some embodiments. The Gaussian waveform with the biggest cross-correlation coefficient was considered the best-fit waveform.

A mathematical function shaped like a cone—with higher value in the center and lower values in the surround—can be used to characterize and quantify the focal thinning and focal bulging[25] caused by keratoconus. An example of such mathematical function is a 2-D Gaussian waveform. The depth and width of focal thinning (or the "cone") of the corneal epithelium were quantified by fitting a cone-shaped mathematical function to the epithelial thickness map or its variables. An example of the epithelial thickness variable is the inverse normalized epithelial thickness maps. The inverse normalized epithelial thickness map is the normal reference (mean epithelial thickness map of normal eyes) divided by the epithelial thickness map under examination. Any focal thinning in keratoconic eyes would appear to be a distinct peak. The fitted mathematical function was centered at the point with maximum or minimum magnitude and the width was adjusted to maximize the cross-correlation between the fitted mathematical function and the inverse normalized epithelial thickness map. The mathematical function with the biggest cross-correlation coefficient was considered the best-fit waveform (FIG. 11).

For the example shown here, the magnitude of the focal thinning is 0.40, which means the epithelial at that point is about 40% thinner than normal. The width (full-width-half-maximum) of the focal thinning is 2.12 mm.

Combining Anatomic Information For Keratoconus Diagnosis

OCT-based keratoconus diagnosis may be achieved by taking advantage of the more complete capture of anatomic information because mathematical cone-fitting is a powerful approach to combine anatomic information. In keratoconus, anterior and posterior bulging, epithelial thinning, and corneal thinning all occur in approximately the same place. Therefore their associated mathematical function should coincide in location and accumulate into a greater peak when added.

Preferably, a composite cone-measure can be obtained using Equation 5 in which the component functions (Gaussian functions are used here as an example) are combined together to form a total function via element-by-element multiplication:

$$G_{total}(x,y) = G_{anterior}(x,y) \cdot G_{posterior}(x,y) \cdot G_{pachymetry}(x,y) \cdot G_{epithelium}(x,y)$$

Equation 5 where $G_{anterior}(x,y)$, $G_{posterior}(x,y)$, $G_{pachymetry}(x,y)$, and $G_{epithelium}(x,y)$ are the best-fit functions for anterior topography, posterior topography, pachymetry and epithelial thickness maps, respectively. $G_{total}(x,y)$ is the overall function. However, in other embodiments, $G_{total}(x,y)$ may be calculated using two or more, but more preferably 3 or more functions selected from the fitted mathematical functions for anterior topography, posterior topography, pachymetry and epithelial thickness maps.

Alternative implementation of combining anatomical information may include combining the component waveform functions by addition. The component waveform functions may also be grouped based on common anatomic features so as to facilitate computation of separate composite cone-measures among groups.

The following example is provided in order to demonstrate and further illustrate certain embodiments and aspects of the present invention and is not to be construed as limiting the scope thereof.

EXAMPLE

Corneal Epithelial Thickness Mapping in Normal and Keratoconic Eyes with Fourier-Domain Optical Coherence Tomography One purpose of this example is to map corneal epithelial thickness in normal and keratoconic eyes with optical coherence tomography (OCT).

Methods.

A Fourier-domain OCT system with 26,000 axial-scans/second scan speed and 5 µm axial resolution was used. A pachymetry scan pattern (8 radials, 1024 axial-scans each, 6 mm diameter) centered at the pupil center was used to image the cornea. A computer algorithm was developed to generate the epithelial thickness (tear film included) map automatically.

The map was divided into 3 zones by diameter: central 2 mm, superior 2-5 mm, and inferior 2-5 mm. The average epithelial thickness from each zone was calculated. Normal and keratoconic eyes (24 eyes each) were scanned 3 times. The repeatability of the measurement was evaluated by pooled standard deviation (SD).

Results.

The central, superior, and inferior epithelial thickness averages (±population SD) were 55.7±1.7, 52.8±2.4, 54.2±2.0 µm in normal eyes and 53.6±4.8, 54.8±4.7, 52.8±4.4 µm in keratoconic eyes. The central epithelial thickness in normal eyes was thicker than those of keratoconic eyes (mean difference 2.1 µm, t-test p=0.05). The epithelium was thinner superiorly than inferiorly in normal eyes (mean difference−1.4±1.1 µm, p<0.001) while thicker superiorly than inferiorly in keratoconic eyes (2.0±4.1 µm, p=0.02). The repeatability of epithelial thickness measurements was better in normal eyes (central 0.5 µm, superior 0.7 µm, inferior 0.6 µm) than those of keratoconus (1.0, 1.2, 1.4 µm).

Conclusion.

High-resolution high-speed FD-OCT is able to map the conical epithelial thickness in normal and keratoconic eyes with excellent reproducibility. The epithelial thickness asymmetry pattern may be useful to identify keratoconic corneas from the normal.

The foregoing detailed description has set forth various embodiments of the devices and/or processes via the use of algorithms, diagrams, flowcharts, and/or examples. Insofar as such algorithms, diagrams, flowcharts, and/or examples contain one or more functions and/or operations, it will be understood by those within the art that each function and/or operation within such block diagrams, flowcharts, or examples can be implemented, individually and/or collectively, by a range of hardware, software, firmware, or combinations thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms.

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

While various aspects and embodiments have been disclosed herein, other aspects and embodiments will be apparent to those of ordinary skill in the art. The various aspects and embodiments disclosed herein are for purposes of illustration and are not intended to be limiting, with the true scope and spirit being indicated by the following claims. Those ordinarily skilled in the art will recognize, or be able to ascertain using no more than routine experimentation, many equivalents to the specific embodiments of the method and compositions described herein. Such equivalents are intended to be encompassed by the claims.

REFERENCES

The entire disclosure of each reference cited herein or listed below is relied upon and incorporated by reference herein.
1. NIshida T, Saika S. Cornea and Sclera: Anatomy and Physiology. In: Krachmer J, Mannis M, Holland E, eds. Cornea, 3rd ed, 2011; v. 1.
2. Hanna C, O'Brien J E. Cell production and migration in the epithelial layer of the cornea. Arch Ophthalmol 1960; 64:536-9.
3. Huang D, Tang M, Shekhar R. Mathematical model of corneal surface smoothing after laser refractive surgery. Am J Ophthalmol 2003; 135(3):267-78.
4. Patel S, Marshall J, Fitzke F W, 3rd. Refractive index of the human corneal epithelium and stroma. J Refract Surg 1995; 11(2):100-5.
5. Haque S, Jones L, Simpson T. Thickness mapping of the cornea and epithelium using optical coherence tomography. Optom Vis Sci 2008; 85(10):E963-76.

6. Li H F, Petroll W M, Moller-Pedersen T, et al. Epithelial and corneal thickness measurements by in vivo confocal microscopy through focusing (CMTF). Curr Eye Res 1997; 16(3):214-21.
7. Patel S V, McLaren J W, Hodge D O, Bourne W M. Confocal microscopy in vivo in corneas of long-term contact lens wearers. Invest Ophthalmol Vis Sci 2002; 43(4):995-1003.
8. Reinstein D Z, Archer T J, Gobbe M. Corneal epithelial thickness profile in the diagnosis of keratoconus. J Refract Surg 2009; 25(7):604-10.
9. Reinstein D Z, Archer T J, Gobbe M. Stability of LASIK in topographically suspect keratoconus confirmed non-keratoconic by Artemis VHF digital ultrasound epithelial thickness mapping: 1-year follow-up. J Refract Surg 2009; 25(7):569-77.
10. Reinstein D Z, Gobbe M, Archer T J, et al. Epithelial, stromal, and total corneal thickness in keratoconus: three-dimensional display with artemis very-high frequency digital ultrasound. J Refract Surg 2010; 26(4):259-71.
11. Reinstein D Z, Silverman R H, Coleman D J. High-frequency ultrasound measurement of the thickness of the corneal epithelium. Refract Corneal Surg 1993; 9(5):385-7.
12. Reinstein D Z, Silverman R H, Raevsky T, et al. Arc-scanning very high-frequency digital ultrasound for 3D pachymetric mapping of the corneal epithelium and stroma in laser in situ keratomileusis. J Refract Surg 2000; 16(4):414-30.
13. Reinstein D Z, Silverman R H, Rondeau M J, Coleman D J. Epithelial and corneal thickness measurements by high-frequency ultrasound digital signal processing. Ophthalmology 1994; 101(1):140-6.
14. Huang D, Swanson E A, Lin C P, et al. Optical coherence tomography. Science 1991; 254(5035):1178-81.
15. Li Y, Shekhar R, Huang D. Corneal pachymetry mapping with high-speed optical coherence tomography. Ophthalmology 2006; 113(5):792-9 e2.
16. Li E Y, Mohamed S, Leung C K, et al. Agreement among 3 methods to measure corneal thickness: ultrasound pachymetry, Orbscan II, and Visante anterior segment optical coherence tomography. Ophthalmology 2007; 114 (10):1842-7.
17. Christopoulos V, Kagemann L, Wollstein G, et al. In vivo corneal high-speed, ultra high-resolution optical coherence tomography. Arch Ophthalmol 2007; 125(8):1027-35.
18. Yasuno Y, Madjarova V D, Makita S, et al. Three-dimensional and high-speed swept-source optical coherence tomography for in vivo investigation of human anterior eye segments. Opt. Express 2005; 13(10652-10664).
19. Huang D, Izatt J A, Yasuno Y, de Boer J F. Future direction of anterior segment optical coherence tomography. In: Steinert R F, Huang D, eds. Anterior segment optical coherence tomography: SLACK, Inc., 2008.
20. Li Y, Tang M L, Zhang X B, et al. Pachymetric mapping with Fourier-domain optical coherence tomography. Journal of Cataract and Refractive Surgery 2010; 36(5):826-31.
21. Jiang T, Merickel M B. Identification and boundary extraction of blobs in complex imagery. Comput Med Imaging Graph 1989; 13(5):369-82.
22. Ambrosio R, Jr., Alonso R S, Luz A, Coca Velarde L G. Corneal-thickness spatial profile and corneal-volume distribution: tomographic indices to detect keratoconus. J Cataract Refract Surg 2006; 32(11):1851-9.
23. Binder P S, Lindstrom R L, Stulting R D, et al. Keratoconus and corneal ectasia after LASIK. J Cataract Refract Surg 2005; 31(10:2035-8.
24. Randleman J B, Woodward M, Lynn M J, Stulting R D. Risk assessment for ectasia after corneal refractive surgery. Ophthalmology 2008; 115(1):37-50.
25. Tang M, Shekhar R, Huang D. Mean curvature mapping for detection of corneal shape abnormality. IEEE Trans Med Imaging 2005; 24(3):424-8.
26. Li Y, Meisler D M, Tang M, et al. Keratoconus diagnosis with optical coherence tomography pachymetry mapping. Ophthalmology 2008; 115(142159-66.
27. Tipping M. The Relevance Vector Machine. In: Solla S, Leen T, Müller K, eds. Advances in Neural Information Processing Systems The MIT Press, 2000.

What is claimed is:

1. An automated non-contact method for mapping a corneal epithelial thickness of an eye a subject, comprising:
   generating corneal images of the subject by scanning the subject's corneal epithelium with a Fourier-domain optical coherence tomography imaging device configured to scan the corneal epithelium with a predetermined scanning pattern wherein a scan is repeated multiple times with the same scanning pattern;
   analyzing the scanned images, via a processor, to identify a structural boundaries of the cornea, wherein the analyzing step by the processor comprises an iterative process of:
   a. checking image quality of each scanned image, and accepting the image for further processing only when the image passes the quality check;
   b. identifying anterior corneal boundary on the image;
   c. aligning, registering and averaging repeated scans;
   d. identifying the epithelial boundary;
   e. identifying the posterior corneal boundary;
   f. dewarping the image to remove distortions; and
   g. repeating steps a through e until all images have been analyzed; and
   generating a corneal epithelial thickness map using the processor based on said identified structural boundaries, and
   displaying the generated corneal epithelial thickness map.

2. The method of claim 1, further including a step of evaluating a corneal epithelium property for non-uniformity.

3. The method of claim 1, wherein said scanning pattern is a radial spoke pattern having N radial scans arranged in a radial spoke line pattern wherein:
   N is an even number equal to or greater than 4;
   said radial spoke lines are evenly distributed 180/N degree apart; and
   each radial scan contains equal number of axial scans.

4. The method of claim 3, wherein said radial scans each has a minimum of 512 axial scans.

5. The method of claim 3, wherein N is 8 and said scanning pattern is repeated at least 3 times in each scan.

6. The method of claim 1, wherein said scanning pattern is a raster scan pattern with evenly distributed line scans.

7. The method of claim 1, wherein said scanning pattern is centered at the pupil center or corneal vertex.

* * * * *